US009482647B2

(12) United States Patent
Isom et al.

(10) Patent No.: US 9,482,647 B2
(45) Date of Patent: Nov. 1, 2016

(54) GEAR FAULT DETECTION

(71) Applicant: Sikorsky Aircraft Corporation, Stratford, CT (US)

(72) Inventors: Joshua D. Isom, Allentown, PA (US); Zaffir A. Chaudhry, South Glastonbury, CT (US); Guicai Zhang, Minhang District (CN); Fanping Sun, Glastonbury, CT (US); Madhusudana Shashanka, Manchester, CT (US); Yan Chen, South Windsor, CT (US)

(73) Assignee: SIKORSKY AIRCRAFT CORPORATION, Stratford, CT (US)

( * ) Notice: Subject to any disclaimer, the term of this patent is extended or adjusted under 35 U.S.C. 154(b) by 462 days.

(21) Appl. No.: 14/035,227

(22) Filed: Sep. 24, 2013

(65) Prior Publication Data
US 2015/0088435 A1 Mar. 26, 2015

(51) Int. Cl.
*G01M 13/02* (2006.01)
*G01N 29/46* (2006.01)
*G01N 29/14* (2006.01)

(52) U.S. Cl.
CPC ............ *G01N 29/46* (2013.01); *G01M 13/021* (2013.01); *G01M 13/028* (2013.01); *G01N 29/14* (2013.01); *G01N 2291/2696* (2013.01)

(58) Field of Classification Search
CPC .................................................. G01M 13/021
USPC ........................................................... 702/35
See application file for complete search history.

(56) References Cited

U.S. PATENT DOCUMENTS

| | | | |
|---|---|---|---|
| 3,277,695 A | 10/1966 | Joline | |
| 3,699,806 A | 10/1972 | Weichbrodt | |
| 5,895,857 A | 4/1999 | Robinson et al. | |
| 6,507,789 B1 | 1/2003 | Reddy et al. | |
| 6,526,356 B1 | 2/2003 | DiMaggio et al. | |
| 6,681,634 B2 | 1/2004 | Sabini et al. | |
| 6,901,335 B2 | 5/2005 | Wang et al. | |
| 7,317,994 B2 | 1/2008 | Iyer et al. | |
| 7,318,007 B2 | 1/2008 | Barkhoudarian | |
| 8,473,252 B2 | 6/2013 | Kar et al. | |
| 8,544,331 B2 * | 10/2013 | Liang ..................... | G01N 29/14 73/659 |
| 2003/0074159 A1* | 4/2003 | Bechhoefer ............ | G01H 1/003 702/181 |
| 2004/0200283 A1 | 10/2004 | Blunt | |
| 2010/0256932 A1 | 10/2010 | Kar | |
| 2013/0180319 A1 | 7/2013 | Klein-Hitpass et al. | |

FOREIGN PATENT DOCUMENTS

WO 2011156196 A2 12/2011

OTHER PUBLICATIONS

International Search Report for application PCT/US2014/057136, dated Dec. 24, 2014, 9 pages.

\* cited by examiner

*Primary Examiner* — Bryan Bui
(74) *Attorney, Agent, or Firm* — Cantor Colburn LLP

(57) ABSTRACT

Embodiments are directed to obtaining an impact energy signal associated with each of a plurality of teeth of a gear over a revolution of a shaft associated with the gear, generating, by a computing device comprising a processor, a profile of the impact energy signal, and declaring a fault associated with an identified tooth included in the plurality of teeth based on an analysis of the profile.

14 Claims, 5 Drawing Sheets

GEAR FAULT DETECTION

BACKGROUND

Gear teeth may be subjected to degradation. Such degradation may be due to any number of factors, such as defects in manufacturing, a breakdown of materials due to use, etc. Current techniques use statistical or time-series features of a time-synchronous average associated with a shaft for a gear of interest. These techniques can detect major faults, but don't typically perform well for earlier stages of gear degradation.

A split torque gearbox (e.g., a planetary gearbox) may share a load among multiple load paths (e.g., multiple parallel load paths). A split torque gearbox may incorporate identical or substantially similar shaft/gear configurations in parallel. Monitoring a vibration associated with split torque gearboxes may be difficult because there may be many identical or substantially similar gear meshes (e.g., the same number of gear teeth, the same shaft frequency). A vibration signal produced by a single faulty gear may be obscured by other healthy gears with, e.g., identical gear mesh frequencies, which can make it difficult to detect and diagnose incipient failures.

BRIEF SUMMARY

An embodiment is directed to a method including: obtaining an impact energy signal associated with each of a plurality of teeth of a gear over a revolution of a shaft associated with the gear, generating, by a computing device comprising a processor, a profile of the impact energy signal, and declaring a fault associated with an identified tooth included in the plurality of teeth based on an analysis of the profile.

An embodiment is directed to an apparatus including: at least one processor, and memory having instructions stored thereon that, when executed by the at least one processor, cause the apparatus to: obtain an impact energy signal associated with each of a plurality of teeth of a gear over a revolution of a shaft associated with the gear, generate a profile of the impact energy signal, and declare a fault associated with an identified tooth included in the plurality of teeth based on an analysis of the profile.

Additional embodiments are described below.

BRIEF DESCRIPTION OF THE DRAWINGS

The present disclosure is illustrated by way of example and not limited in the accompanying figures in which like reference numerals indicate similar elements.

DETAILED DESCRIPTION

Figure 1:
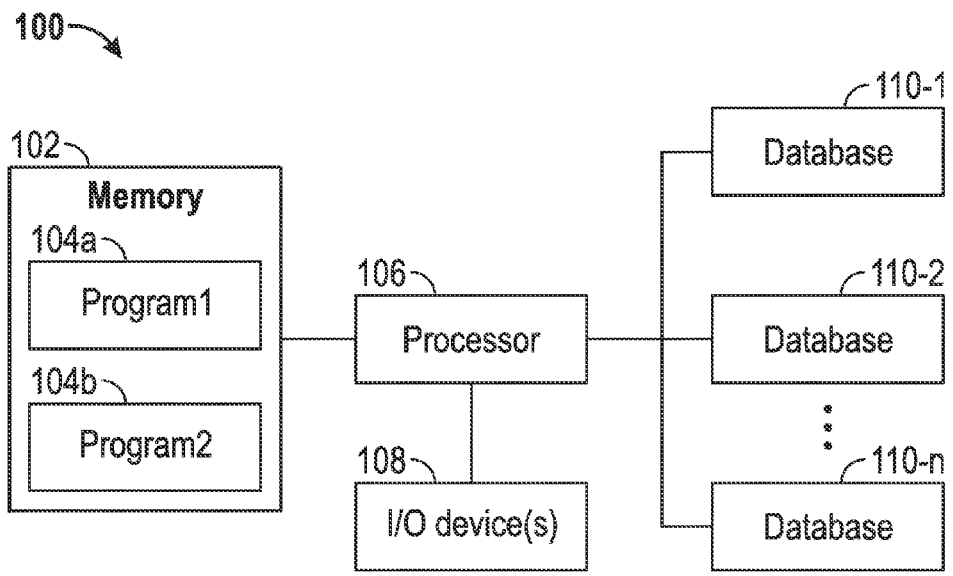
FIG. 1 is a schematic block diagram illustrating an exemplary computing system.

It is noted that various connections are set forth between elements in the following description and in the drawings (the contents of which are included in this disclosure by way of reference). It is noted that these connections in general and, unless specified otherwise, may be direct or indirect and that this specification is not intended to be limiting in this respect. In this respect, a coupling between entities may refer to either a direct or an indirect connection.

Exemplary embodiments of apparatuses, systems, and methods are described for obtaining data regarding the status or health of a gear. Such data may be analyzed at the level of a tooth of the gear. In some embodiments, a profile of a gear may be analyzed to determine if an abnormality exists with respect to the profile. When such an abnormality does exist, a determination may be made that it is likely that a tooth of the gear is degraded.

Referring to FIG. 1, an exemplary computing system 100 is shown. The system 100 is shown as including a memory 102. The memory 102 may store executable instructions. The executable instructions may be stored or organized in any manner and at any level of abstraction, such as in connection with one or more applications, processes, routines, procedures, methods, etc. As an example, at least a portion of the instructions are shown in FIG. 1 as being associated with a first program 104a and a second program 104b.

The instructions stored in the memory 102 may be executed by one or more processors, such as a processor 106. The processor 106 may be coupled to one or more input/output (I/O) devices 108. In some embodiments, the I/O device(s) 108 may include one or more of a keyboard or keypad, a touchscreen or touch panel, a display screen, a microphone, a speaker, a mouse, a button, a remote control, a control stick, a joystick, a printer, a telephone or mobile device (e.g., a smartphone), etc. The I/O device(s) 108 may be configured to provide an interface to allow a user to interact with the system 100.

As shown, the processor 106 may be coupled to a number 'n' of databases, 110-1, 110-2, . . . 110-n. The databases 110 may be used to store data. In some embodiments, the data may be associated with a gear. The processor 106 may be operative on the data to generate a profile for the gear.

The system 100 is illustrative. In some embodiments, one or more of the entities may be optional. In some embodiments, additional entities not shown may be included. For example, the system 100 may be part of a network. In some embodiments, the entities may be arranged or organized in a manner different from what is shown in FIG. 1. For example, in some embodiments, the memory 102 may be coupled to or combined with one or more of the databases 110.

Figure 2:
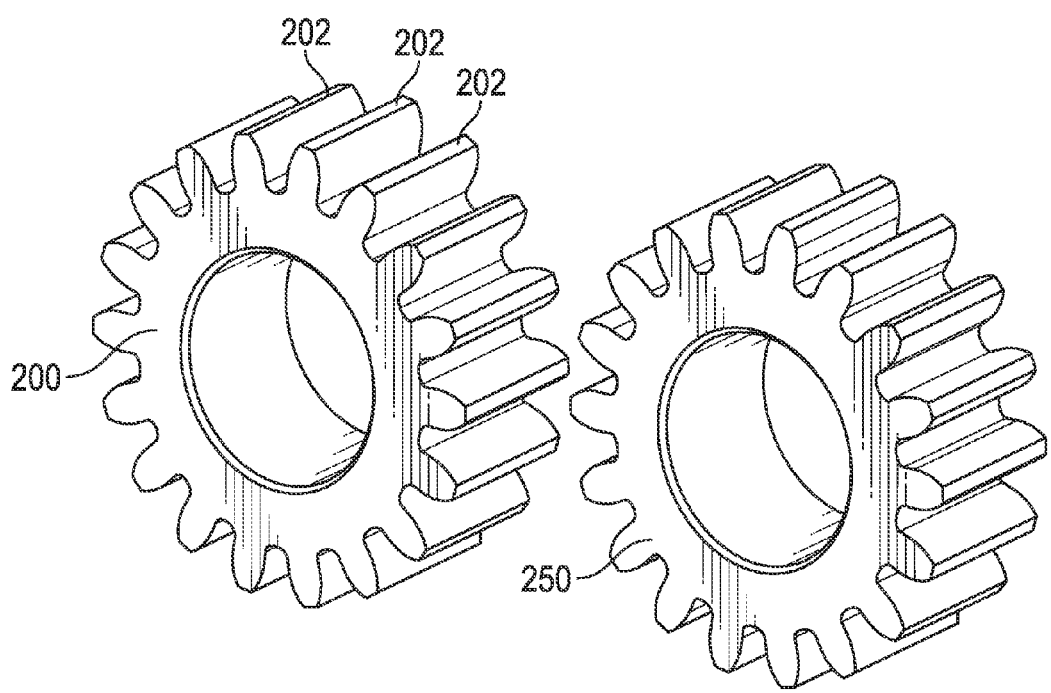
FIG. 2 illustrates exemplary gears.

Referring now to FIG. 2, an exemplary gear 200 is shown. The gear 200 is shown as including a number of teeth. A few of the teeth are labeled as 202 in FIG. 2. The gear 200 may mate with or mesh with an additional gear 250.

The gears 200 and 250 are illustrative. In some embodiments, a gear may be of a different size or dimension than the gear 200 or the gear 250. In some embodiments, a gear may include more or fewer teeth than the gear 200 or the gear 250. All types of gears may be used, including a helical gear, a bevel gear, etc.

Figure 3:
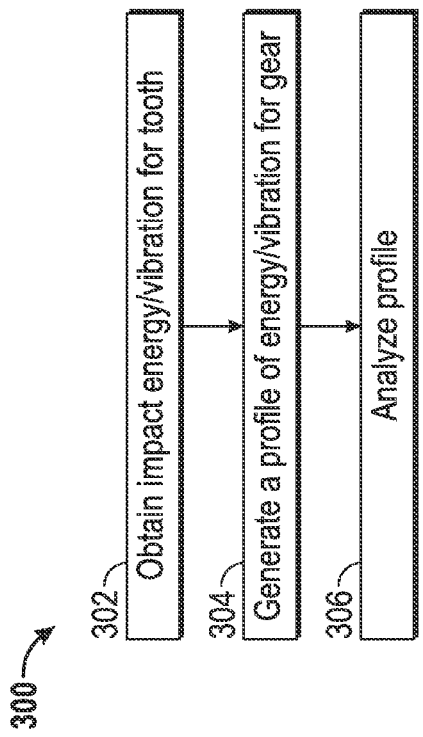
FIG. 3 illustrates a flow chart of an exemplary method.

Turning now to FIG. 3, a flow chart of an exemplary method 300 is shown. The method 300 may be executed by one or more systems, components, or devices, such as those described herein (e.g., the system 100). The method 300 may be used to generate a profile for a gear (e.g., gear 200). An analysis of the profile may be able to pinpoint a tooth of the gear that is likely degraded.

In block 302, a gear may be turned or rotated. As a tooth of the gear comes into contact with or meshes with, e.g., a tooth of a second gear (e.g., gear 250), an impact energy or vibration may be experienced by the tooth of the gear. This energy/vibration signal may be obtained and stored in a database or memory. The signal may be segmented into a number of segments equal to the number of teeth associated with the gear. The impact energy of block 302 may be related to actual, physical energy. The impact energy may be obtained from FIG. 6, described further below.

Block 302 may repeat for each tooth of the gear.

In block 304, a profile may be generated based on the measurements of block 302. The profile may correspond to the energy or vibration experienced by the gear over time. When a tooth of the gear impacts, e.g., a tooth of the second gear, there may be a relatively large spike in terms of the energy/vibration.

In block 306, the profile may be analyzed to determine if any anomalies exist. For example, if the teeth of the gear are similarly constructed/situated, the profile may demonstrate a consistent or recognizable pattern characterized by relatively large spikes in terms of energy/vibration when the teeth of the gear come into contact with the teeth of the second gear, followed by relatively low amounts of energy/vibration. If the profile deviates from a consistent pattern in an amount greater than a threshold then it may be probable that the associated tooth is degraded (e.g., it may be likely that the tooth is degraded in an amount greater than a threshold) and a fault may be declared.

The deviation may correspond to a deviation in terms of amplitude or magnitude. For example, if a particular tooth of the gear is degraded, that particular tooth may experience an impact energy/vibration that is substantially less than or greater than the impact energies/vibrations experienced by the other teeth of the gear. The deviation may correspond to a deviation in terms of time. For example, if a particular tooth of the gear is degraded, that particular tooth may experience an impact energy/vibration that is skewed relative to the timing of the impact energies/vibrations experienced by the other teeth of the gear.

As part of block 306, an empirical estimate of expected tooth impact energy may be generated for each tooth of the gear. The empirical estimate may be generated using the energy of impact of neighboring teeth, potentially based on an averaging of the energy produced by neighboring teeth or a cubic spline fit. If the measured/calculated impact energy is significantly different than the estimate derived from neighboring teeth, a gear tooth fault may be declared.

The method 300 is illustrative. In some embodiments, one or more of the blocks or operations (or a portion thereof) may be optional. In some embodiments, additional operations not shown may be included. In some embodiments, the operations may execute in an order or sequence different from what is shown in FIG. 3.

Figure 4:
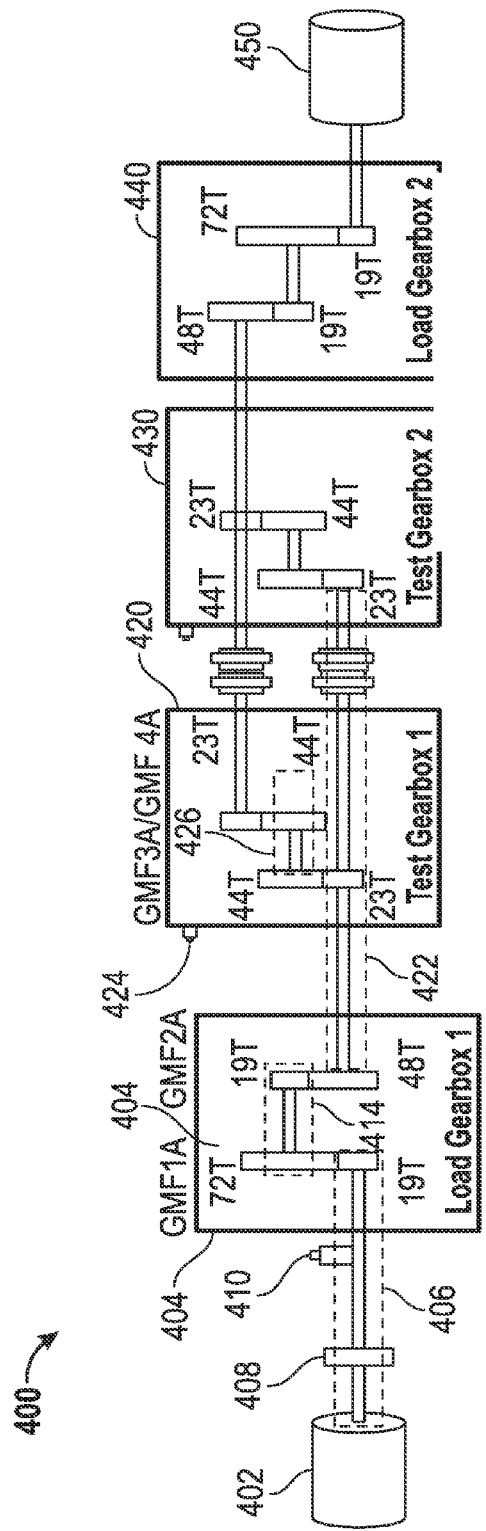
FIG. 4 illustrates a block diagram of an exemplary system.

Referring now to FIG. 4, a system 400 is shown. The system 400 may be used to provide separation in terms of a gearbox vibration source.

As shown in FIG. 4, a drive motor 402 may be coupled to a first load gearbox 404 via a motor shaft 406. The motor shaft may include, or be coupled to, an encoder 408 and a tachometer 410.

The first load gearbox 404 may include, or be coupled to, an idler shaft 414.

The first load gearbox 404 may be coupled to a first test gearbox 420, potentially by way of an input shaft 422. The first test gearbox 420 may include, or be coupled to, an accelerometer 424. The first test gearbox 420 may include, or be coupled to, an idler shaft 426.

The first test gearbox 420 may be coupled to a second test gearbox 430. As a part of such coupling, the input shaft 422 may extend between the first test gearbox 420 and the second test gearbox 430.

The second test gearbox 430 may be coupled to a load gearbox 440.

The load gearbox 440 may be coupled to a load motor 450.

As shown in FIG. 4, the first load gearbox 404, the first test gearbox 420, the second test gearbox 430, and the second load gearbox 440 may include a number of gears. For example, the motor shaft 406 may be coupled to the first load gearbox 404 by way of a first gear having, e.g., nineteen teeth (19T). That first gear may, in turn, be coupled to a second gear having, e.g., seventy-two teeth (72T). That second gear may, in turn, be coupled to the idler shaft 414, and the idler shaft 414 may be coupled to a third gear having, e.g., nineteen teeth (19T). That third gear may, in turn, be coupled to a fourth gear having, e.g., forty-eight teeth (48T).

Figure 5:
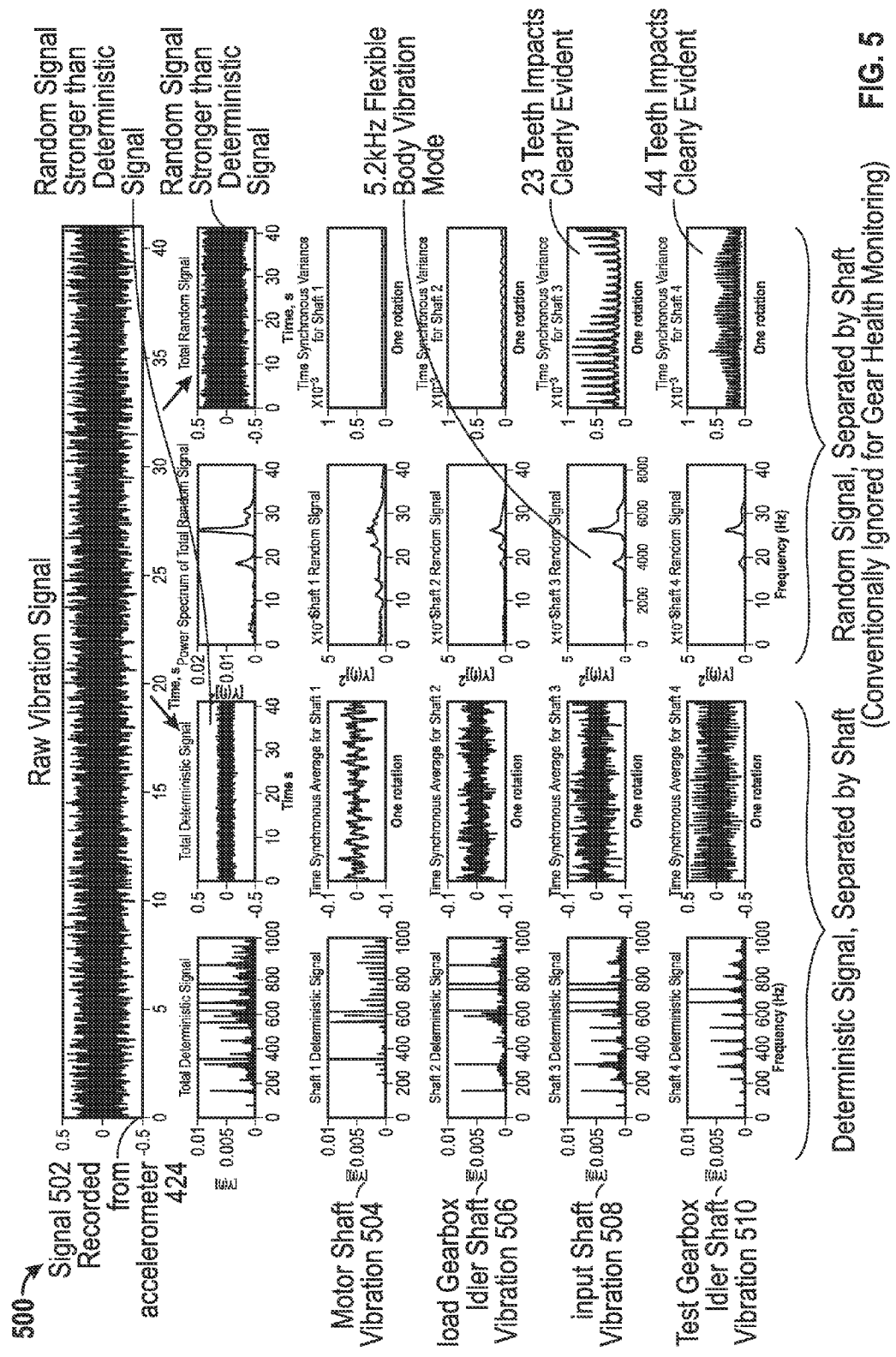
FIG. 5 illustrates exemplary waveforms.

Referring now to FIG. 5, a number of exemplary waveforms 500 are shown. The waveforms 500 may be generated based on the use of the system 400. As shown in FIG. 5, the waveforms 500 may be separated by a shaft into deterministic waveforms or signals and random waveforms or signals. The random waveforms may be conventionally ignored for purposes of monitoring gear health.

A first of the waveforms 500, denoted as a waveform 502, may correspond to a signal recorded by the accelerometer 424. As shown in FIG. 5, the random portion of the signal 502 may be stronger than the deterministic portion of the signal 502.

A second of the waveforms 500, denoted as a waveform 504, may correspond to vibration of the motor shaft 406.

A third of the waveforms 500, denoted as a waveform 506, may correspond to vibration of the idler shaft 414.

A fourth of the waveforms 500, denoted as a waveform 508, may correspond to a vibration of the input shaft 422. As shown in FIG. 5, a 5.2 kHz flexible body vibration mode may be experienced in the input shaft vibration 508. Over one rotation of the input shaft 422, twenty-three teeth (23T) impacts may be clearly evident.

A fifth of the waveforms 500, denoted as a waveform 510, may correspond to a vibration of the idler shaft 426. As shown in FIG. 5, over one rotation of the idler shaft 426, forty-four teeth (44T) impacts may be clearly evident.

Figure 6:
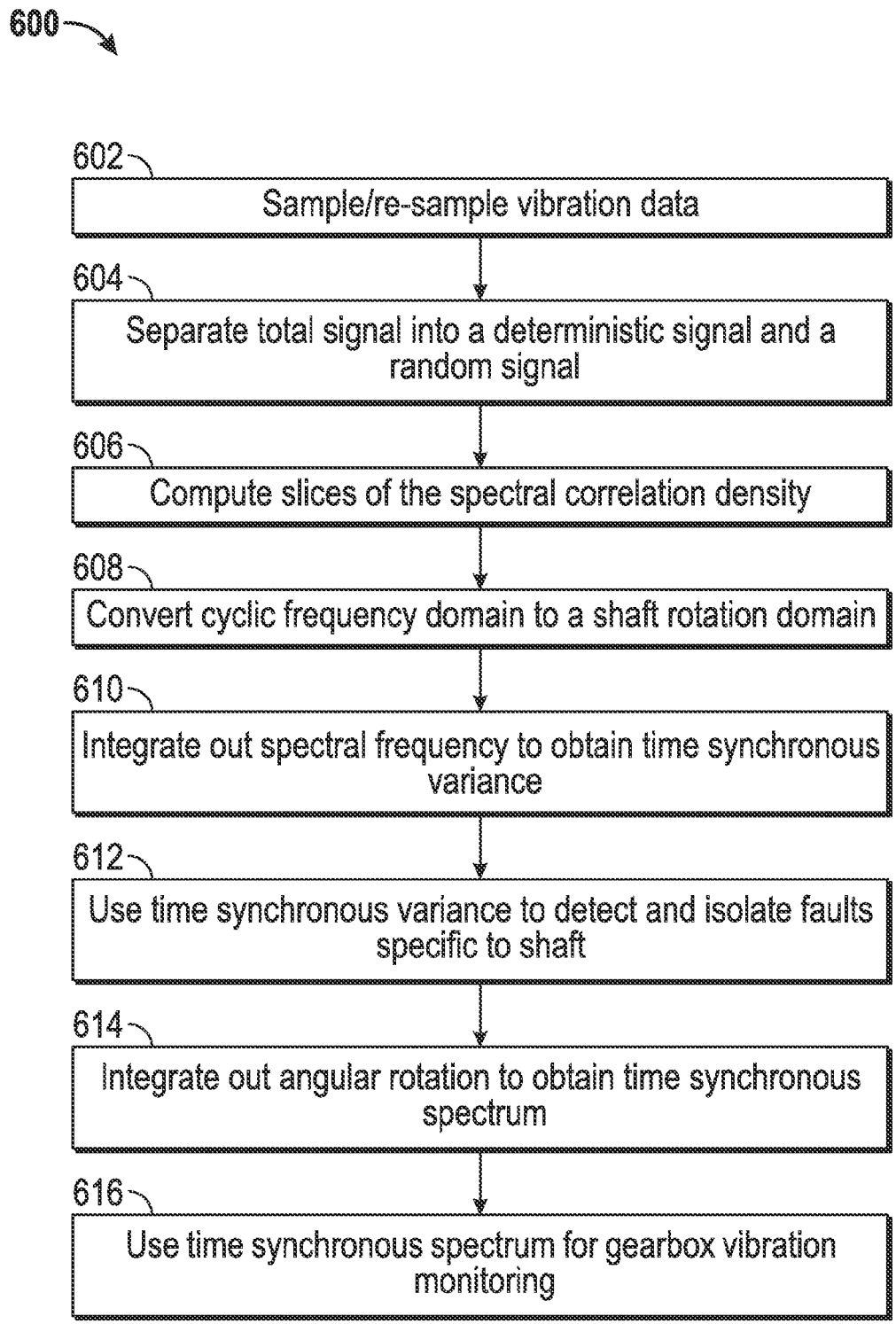
FIG. 6 illustrates a flow chart of an exemplary method.

Referring now to FIG. 6, a flow chart of an exemplary method 600 is shown. The method 600 may be executed by one or more systems, components, or devices, such as those described herein (e.g., the system 100, the system 400). The method 600 may be used to isolate a deterministic vibration associated with a particular gearbox shaft. In this respect, the method 600 may be executed for each shaft of interest.

In block 602, vibration data may be sampled, or resampled, so that the vibration data has a constant sampling rate in terms of shaft angular rotation, rather than time.

In block 604, a total signal corresponding to the vibration data may be separated into a deterministic signal and a random signal.

In block 606, slices of the spectral correlation density may be computed at the fundamental frequency and its integer multiples for the shaft, up to a sufficiently large multiple (e.g., a multiple in an amount greater than a threshold in order to obtain a good resolution), which may be based on the random signal obtained in block 604. The multiples may include several multiples of a gear mesh order.

In block 608, a cyclic frequency domain may be converted to a shaft rotation (pseudo-time) domain using an inverse Fourier transform to produce a time-frequency representation (Wigner-Ville spectrum) for the shaft over one shaft revolution.

In block 610, the spectral frequency may be integrated out of the Wigner-Ville spectrum to obtain a time synchronous variance. The time synchronous variance may correspond to a measure, over one revolution, of the random energy or impact energy produced by the shaft rotation as a function of rotation angle.

In block 612, features of the time synchronous variance may be used to detect and isolate faults specific to the shaft.

In block 614, the angular rotation may be integrated out of the Wigner-Ville spectrum to obtain a time synchronous spectrum. The time synchronous spectrum may correspond to an estimate of the power spectrum associated with a random vibration produced by the shaft. The time synchronous spectrum may correspond to the plots labeled as "Shaft 'X' Random Signal" in FIG. 5, where 'X' is a number.

In block 616, features of the time synchronous spectrum may be used for gearbox vibration monitoring.

The method 600 is illustrative. In some embodiments, one or more of the blocks or operations (or a portion thereof) may be optional. In some embodiments, additional operations not shown may be included. In some embodiments, the operations may execute in an order or sequence different from what is shown in FIG. 6.

The method 600 may be used to isolate random vibration specific to a gearbox shaft in a manner that is analogous to the time synchronous average. The ability to isolate the random vibration specific to a shaft may allow for improved detection and isolation of faults associated with microscopic phenomena, such as rubbing, wear, pitting, etc.

The method 600 may be used to obtain a residual or random signal. For example, a total signal may effectively be deconstructed into a time synchronous average signal and the random signal. The random signal may be analyzed or processed to obtain an energy history associated with the meshing of gear teeth.

As described above, it can be difficult to detect and diagnose incipient failures in connection with split torque gearboxes. Gear mesh impulses may produce a decaying random signal associated with the reflection of mechanical waves in a gearbox structure. The signal may have a carrier frequency that may be equal to the speed of the wave in the material divided by a characteristic length. The characteristic length may be determined by the geometry of the gearbox and the placement or location of an accelerometer. Gears that are otherwise identical may have different characteristic lengths and carrier frequencies when measured at a single accelerometer location.

Figure 7:
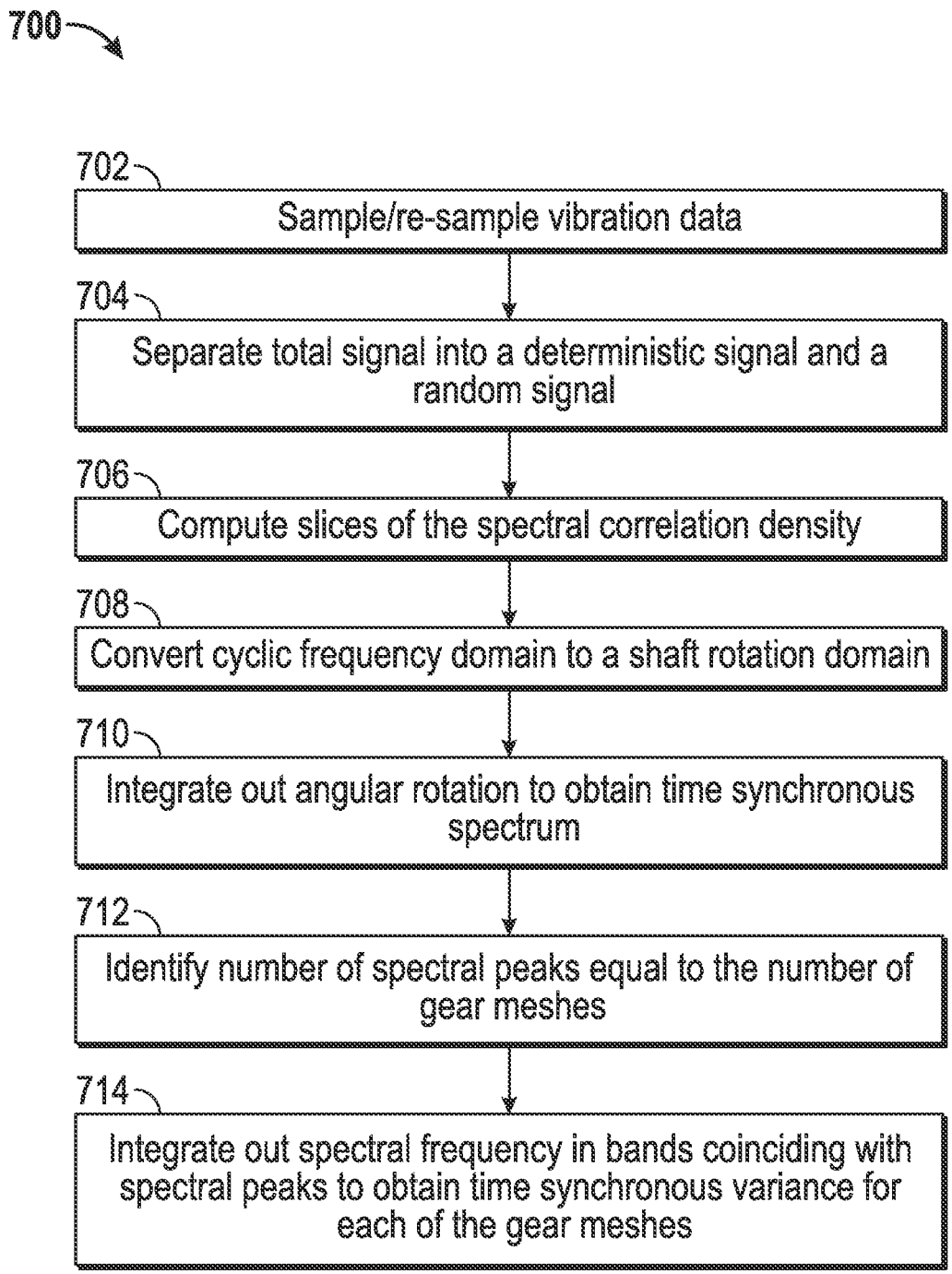
FIG. 7 illustrates a flow chart of an exemplary method.

Referring now to FIG. 7, a flow chart of an exemplary method 700 is shown. The method 700 may be executed by one or more systems, components, or devices, such as those described herein. The method 700 may be used to compute a time synchronous variance for each of identical or similar gear meshes.

In block 702, vibration data may be sampled, or re-sampled, so that the vibration data has a constant sampling rate in terms of shaft angular rotation, rather than time.

In block 704, a total signal corresponding to the vibration data may be separated into a deterministic signal and a random signal.

In block 706, slices of the spectral correlation density may be computed at the fundamental frequency and its integer multiples for a shaft, up to a sufficiently large multiple (e.g., a multiple in an amount greater than a threshold in order to obtain a good resolution). The multiples may include several multiples of a gear mesh order.

In block 708, a cyclic frequency domain may be converted to a shaft rotation (pseudo-time) domain using an inverse Fourier transform to produce a time-frequency representation (Wigner-Ville spectrum) for the shaft over one shaft revolution.

In block 710, the angular rotation may be integrated out of the Wigner-Ville spectrum to obtain a time synchronous spectrum. The time synchronous spectrum may correspond to an estimate of the power spectrum associated with a random vibration produced by the shaft.

In block 712, a number of spectral peaks equal to the number of gear meshes may be identified.

In block 714, spectral frequency in bands coinciding with the identified spectral peaks may be integrated out of the Wigner-Ville spectrum to obtain a unique time synchronous variance (energy over one shaft revolution) for each of the gear meshes.

The method 700 is illustrative. In some embodiments, one or more of the blocks or operations (or a portion thereof) may be optional. In some embodiments, additional operations not shown may be included. In some embodiments, the operations may execute in an order or sequence different from what is shown in FIG. 7.

The method 700 may be used to monitor the vibration energy produced by a single gear mesh. The vibration energy may be isolated from a signal produced in conjunction with the other gear meshes.

Illustrative embodiments and examples described herein relate aspects of the disclosure to gears, shafts, and gearboxes. Aspects of this disclosure may be applied in other contexts, such as in connection with bearings.

As described herein, in some embodiments various functions or acts may take place at a given location and/or in connection with the operation of one or more apparatuses, systems, or devices. For example, in some embodiments, a portion of a given function or act may be performed at a first device or location, and the remainder of the function or act may be performed at one or more additional devices or locations.

Embodiments may be implemented using one or more technologies. In some embodiments, an apparatus or system may include one or more processors, and memory storing instructions that, when executed by the one or more processors, cause the apparatus or system to perform one or more methodological acts as described herein. Various mechanical components known to those of skill in the art may be used in some embodiments.

Embodiments may be implemented as one or more apparatuses, systems, and/or methods. In some embodiments, instructions may be stored on one or more computer-readable media, such as a transitory and/or non-transitory computer-readable medium. The instructions, when executed, may cause an entity (e.g., an apparatus or system) to perform one or more methodological acts as described herein.

Aspects of the disclosure have been described in terms of illustrative embodiments thereof. Numerous other embodiments, modifications and variations within the scope and spirit of the appended claims will occur to persons of ordinary skill in the art from a review of this disclosure. For example, one of ordinary skill in the art will appreciate that the steps described in conjunction with the illustrative figures may be performed in other than the recited order, and that one or more steps illustrated may be optional.

What is claimed is:

1. A method comprising:
generating an estimated impact energy signal corresponding to each of a plurality of teeth of a gear over a revolution of a shaft associated with the gear tooth;
obtaining an impact energy signal associated with each of the plurality of teeth;
comparing the estimated impact energy signal with the obtained impact energy signal;
generating, by a computing device comprising a processor, a profile of the impact energy signal; and
declaring a fault associated with at least one tooth of the plurality of teeth, the fault being based on said comparing indicating a deviation between the estimated impact energy signal and the obtained impact energy signal in an amount greater than a threshold.

2. The method of claim 1, further comprising:
segmenting the impact energy signal into a number of segments equal to a number of teeth included in the plurality of teeth; and
integrating each segment included in the number of segments to calculate the total energy released by each gear tooth impact.

3. The method of claim 1, further comprising:
separating the signal into a time synchronous average signal and a random signal; and
processing the random signal to obtain an energy history associated with a meshing of the teeth.

4. The method of claim 1, further comprising:
computing slices of a spectral correlation density associated with the shaft at a fundamental frequency and multiples of the fundamental frequency to obtain a cyclic frequency domain representation; and
converting the cyclic frequency domain representation to a rotation domain to produce a time-frequency representation for the shaft.

5. The method of claim 4, further comprising:
integrating a spectral frequency out of the time-frequency representation to obtain a time synchronous variance; and
using the time synchronous variance to detect and isolate a fault associated with the shaft.

6. The method of claim 4, further comprising:
integrating an angular rotation out of the time-frequency representation to obtain a time synchronous spectrum; and
using the time synchronous spectrum to monitor vibration of a gearbox.

7. The method of claim 4, further comprising:
integrating a spectral frequency out of the time-frequency representation in bands coinciding with identified spectral peaks equal to a number of substantially similar gear meshes; and
using the integrated spectral frequency to obtain a unique time synchronous variance for each of the gear meshes.

8. An apparatus comprising:
at least one processor; and
memory having instructions stored thereon that, when executed by the at least one processor, cause the apparatus to:
generate an estimated impact energy signal corresponding to each tooth of the plurality of teeth;
obtain an impact energy signal associated with each of a plurality of teeth of a gear over a revolution of a shaft associated with the gear;
compare the estimated impact energy signal with the obtained impact energy signal;
generate a profile of the impact energy signal; and
declare a fault associated with at least one of the plurality of teeth, the fault being based on the comparison indicating a deviation between the estimated impact energy signal and the obtained impact energy signal in an amount greater than a threshold.

9. The apparatus of claim 8, wherein the instructions, when executed by the at least one processor, cause the apparatus to:
segment the impact energy signal into a number of segments equal to a number of teeth included in the plurality of teeth, and
integrate each segment included in the number of segments to calculate the total energy released by each gear tooth impact.

10. The apparatus of claim 8, wherein the instructions, when executed by the at least one processor, cause the apparatus to:
separate the impact energy signal into a time synchronous average signal and a random signal, and
process the random signal to obtain an energy history associated with a meshing of the teeth.

11. The apparatus of claim 8, wherein the instructions, when executed by the at least one processor, cause the apparatus to:
compute slices of a spectral correlation density associated with the shaft at a fundamental frequency and multiples of the fundamental frequency to obtain a cyclic frequency domain representation, and
convert the cyclic frequency domain representation to a rotation domain using an inverse Fourier transform to produce a time-frequency representation for the shaft.

12. The apparatus of claim 11, wherein the instructions, when executed by the at least one processor, cause the apparatus to:
integrate a spectral frequency out of the time-frequency representation to obtain a time synchronous variance, and
use the time synchronous variance to detect and isolate a fault associated with the shaft.

13. The apparatus of claim 11, wherein the instructions, when executed by the at least one processor, cause the apparatus to:
integrate an angular rotation out of the time-frequency representation to obtain a time synchronous spectrum, and
use the time synchronous spectrum to monitor vibration of a gearbox associated with the gear and the shaft.

14. The apparatus of claim 11, wherein the instructions, when executed by the at least one processor, cause the apparatus to:
integrate a spectral frequency out of the time-frequency representation in bands coinciding with identified spectral peaks equal to a number of gear meshes, and
use the integrated spectral frequency to obtain a unique time synchronous variance for each of the gear meshes.

* * * * *